US012623024B2

(12) United States Patent
Ricci

(10) Patent No.: US 12,623,024 B2
(45) Date of Patent: May 12, 2026

(54) SYRINGE WITH LUER-LOCK CONNECTOR PROVIDED WITH A TAMPER-PROOF CAP

(71) Applicant: PLATINUM PHARMA SERVICE S.R.L.S., Citta' Sant'angelo (IT)

(72) Inventor: Alfredo Ricci, Citta' Sant'angelo (IT)

(73) Assignee: PLATINUM PHARMA SERVICE S.R.L.S., Citta' Sant'Angelo (IT)

( * ) Notice: Subject to any disclaimer, the term of this patent is extended or adjusted under 35 U.S.C. 154(b) by 413 days.

(21) Appl. No.: 18/558,428

(22) PCT Filed: May 2, 2022

(86) PCT No.: PCT/IB2022/054023
§ 371 (c)(1),
(2) Date: Nov. 1, 2023

(87) PCT Pub. No.: WO2022/234422
PCT Pub. Date: Nov. 10, 2022

(65) Prior Publication Data
US 2024/0216614 A1 Jul. 4, 2024

(30) Foreign Application Priority Data

May 5, 2021 (IT) ......................... 102021000011435

(51) Int. Cl.
*A61M 5/31* (2006.01)
*A61M 5/34* (2006.01)
*A61M 5/50* (2006.01)
(52) U.S. Cl.
CPC .......... *A61M 5/3134* (2013.01); *A61M 5/347* (2013.01); *A61M 5/5086* (2013.01);
(Continued)

(58) Field of Classification Search
CPC ........ A61M 5/3134; A61M 2005/3104; A61M 2005/3106; A61M 5/34; A61M 5/5086; A61M 2205/276; A61M 5/3202
See application file for complete search history.

(56) References Cited

U.S. PATENT DOCUMENTS 6,196,998 B1 * 3/2001 Jansen ................ A61M 5/3134
604/111
10,758,684 B1 9/2020 Mtello et al.
(Continued)

FOREIGN PATENT DOCUMENTS

EP 2823842 A1 1/2015
EP 2832391 A1 2/2015

OTHER PUBLICATIONS

International Search Report and Written Opinion issued on Aug. 5, 2022, in corresponding International Application No. PCT/IB2022/054023, 10 pages.

*Primary Examiner* — Susan S Su
*Assistant Examiner* — Erin A Kim
(74) *Attorney, Agent, or Firm* — Maier & Maier, PLLC

(57) ABSTRACT

A syringe including a hollow cylindrical body containing a product to be injected and from which there extend a hollow tip equipped with a Luer-lock connector and a plunger, sliding inside the hollow cylindrical body; and a tamper-proof cap including a closure cap and a tamper-proof insert, where the closure cap includes a portion for coupling with the Luer-lock connector and a handle portion. An external seat for housing the tamper-proof insert is formed in the handle portion of the main body of the closure cap. The tamper-proof insert includes at least one longitudinal section, a transverse section and a terminal element, which is connected to a free end of the longitudinal section by a frangible connection, the terminal element configured to be immovably housed in a corresponding groove formed on an
(Continued)

external surface of the Luer-lock connector. The tamper-proof insert is immovably coupled to the closure cap.

19 Claims, 5 Drawing Sheets

(52) U.S. Cl.
CPC ............... *A61M 2005/3104* (2013.01); *A61M 2005/3106* (2013.01); *A61M 2205/0227* (2013.01); *A61M 2205/276* (2013.01); *A61M 2205/584* (2013.01)

(56) References Cited

U.S. PATENT DOCUMENTS

| | | | |
|---|---|---|---|
| 2008/0097310 A1* | 4/2008 | Buehler ................. | A61M 5/50 |
| | | | 604/111 |
| 2013/0237911 A1 | 9/2013 | Von Schuckmann | |
| 2017/0354792 A1 | 12/2017 | Ward | |

* cited by examiner

SYRINGE WITH LUER-LOCK CONNECTOR PROVIDED WITH A TAMPER-PROOF CAP

TECHNICAL FIELD

The present invention relates, in general, to the technical field of the syringes with Luer-lock connector. More particularly, the present invention relates to a syringe, preferably of the pre-filled type, with Luer-lock connector equipped with a tamper-proof cap.

BACKGROUND

Syringes, in particular those pre-filled, are widely used to inject, in a person, medicinal products such as, among others, anticoagulants, for example heparin and the like, vaccines, small sized molecules, and cosmetic products, for example hyaluronic acid.

They represent a growing market, as they make it possible to effectively reduce errors in the dosage of a product to be injected and contribute to reduce packaging costs.

A syringe typically comprises a transparent cylindrical body, on which measurement marks are shown, a plunger sliding inside the transparent cylindrical body and a hollow and frusto-conical tip, extending from the transparent cylindrical body and onto which a needle, it also being hollow, is then fitted through which the product to be injected contained in the hollow cylindrical body passes. The plunger is provided, at one of the ends thereof, with a rubber ring or capsule to ensure the controlled and constant sliding of the plunger inside the transparent cylindrical body. The tip of the syringe can be provided with a Luer-lock connector, i.e. a screwing system that locks the needle connection to prevent the unintentional removal thereof. Finally, the syringe is provided with a closure cap, the main function of which is to prevent the product contained in the syringe from leaking.

The closure caps of the syringes with Luer-lock connector, in addition to having sealing properties, i.e. ensuring air tightness, and anti-screwing properties, i.e. being configured so that they do not accidentally and undesirably separate from the syringe when the syringe is not in use, typically during syringe storage, must also ensure that the product contained in the syringe is not tampered with, either accidentally or intentionally, prior to use. In fact, it is essential that the closure cap is only removed from the syringe when it is being used by a healthcare professional to inject a person with the product contained in the syringe. This is done in order to preserve the product, avoiding the introduction or removal of substances other than those with which the syringe is e.g. pre-filled during production, into/from the syringe during transport and storage thereof.

A syringe provided with a tamper-proof cap is disclosed in the patent document no. U.S. Pat. No. 5,135,496.

The syringe comprises a hollow body having a neck centred on an axis, an elastomeric cap, which is inserted into the neck and having an end projecting axially from the neck, and a stiffening sleeve, which is mounted on the cap and on the neck and having a collar mounted around the projecting end of the cap and itself projecting axially forward with respect to the cap. The syringe also comprises an elastomeric cap, which is inserted into the collar, a protective cap, which is mounted on the sleeve and on the cap and having a rear terminal edge, and a ring, which is snap-fittingly fixed on the sleeve and having a front terminal edge facing the rear terminal edge of the protective cap. The rear terminal edge of the protective cap and the front terminal edge of the ring fixed to the sleeve are connected therebetween by a frangible connection, so that the cap is held in place on the syringe body. The cap is thus only removable from the syringe body after the frangible connection has been broken.

However, the tamper-proof syringe system described above has some drawbacks. In particular, this known system is not able to guarantee to the healthcare professional the total absence of tampering with the cap, and therefore the integrity of the product contained in the syringe. In fact, due to the presence of the snap-fitting coupling between the ring, to which the protective cap is connected by the frangible connection, and the sleeve which is mounted on the hollow body of the syringe, it is sufficient to elastically deform the ring to release the latter, and with it the protective cap, from the syringe, and this without breaking the frangible connection between the sleeve and the protective cap. Therefore, when using the syringe, the healthcare professional may not notice that the tamper-proof system has been violated.

Other syringes with tamper-proof cap of the known type include the presence of micro-welds between the cap and external portions of the hollow cylindrical body, or of the Luer-lock connector, of the syringe.

Even these known tamper-proof caps, although structurally and functionally simple, do not guarantee to the healthcare professional the total absence of tampering, and therefore the integrity of the product contained in the syringe. In fact, a third party, by using special tools, could remove the micro-welds between the tamper-proof cap and the syringe, access the product contained in the syringe and then make new micro-welds. As a result, the healthcare professional may once again fail to notice that the tamper-proof cap has been violated.

SUMMARY

The main object of the present invention is therefore to provide a syringe with Luer-lock connector equipped with tamper-proof cap capable of overcoming the drawbacks mentioned above with reference to syringes with a tamper-proof cap of a known type.

More particularly, the main object of the present invention is to provide a syringe with Luer-lock connector equipped with tamper-proof cap, configured to guarantee the total absence of tampering with the cap and therefore the integrity of the product contained in the syringe.

Still another object of the present invention is to provide a syringe with Luer-lock connector equipped with a tamper-proof cap, which is structurally simple and can therefore be easily assembled on the syringe, without the aid of machine tools and/or welding methods, for example ultrasonic welding.

Last but not least, an object of the present invention is to provide a syringe with Luer-lock connector equipped with a tamper-proof cap, which can be produced in a timely manner and at competitive costs.

These and other objects of the present invention are achieved by a syringe with Luer-lock connector equipped with tamper-proof cap incorporating the features of the appended claims, which form an integral part of the present description.

The invention thus relates to a syringe comprising a hollow cylindrical body, containing a product to be injected and from which a hollow tip equipped with Luer-lock connector extends, and a plunger, sliding inside the hollow cylindrical body.

The syringe also comprises a tamper-proof cap, comprising a closure cap and a tamper-proof insert, in which the closure cap includes a portion for coupling with the Luer-lock connector and a handle portion. An external seat for housing the tamper-proof insert is formed in the handle portion.

The tamper-proof insert comprises at least one longitudinal section, a transverse section and a terminal element, which is connected to a free end of the longitudinal section by a frangible connection, the terminal element being configured to be immovably housed in a corresponding groove formed on an external surface of the Luer-lock connector.

The tamper-proof cap further comprises means for the unmovable coupling between the tamper-proof insert and the closure cap.

A tamper-proof cap is formed thanks to this combination of features, in particular thanks to the unmovable coupling mode between the tamper-proof insert and the closure cap and the Luer-lock connector. In fact, since the closure cap and the tamper-proof insert are immovably coupled therebetween, the tamper-proof insert is no longer separable from the closure cap and forms a single body with it. As a result, when the tamper-proof insert is mounted on the closure cap and on the Luer-lock connector of the syringe, it is impossible to tamper with the cap. The only way to unscrew the cap from the syringe is to break the tamper-proof insert at the frangible connection.

In an embodiment, the unmovable coupling means comprise at least one coupling element, which extends from the transverse section of the tamper-proof insert, towards the inside of the tamper-proof insert, in order to be coupled by interference with a corresponding cavity of the closure cap, which extends, preferably longitudinally, towards the inside of the handle portion of the closure cap.

In an embodiment, at least the at least one unmovable coupling element is wedge-shaped or the corresponding cavity of the closure cap has slightly inclined walls.

In an embodiment, the unmovable coupling means comprise at least one hooking element, which extends from the transverse section of the tamper-proof insert, towards the inside of the tamper-proof insert, in order to be snap-fittingly housed in a corresponding cavity of the closure cap, which extends, preferably longitudinally, towards the inside of the handle portion of the closure cap.

In an embodiment, the hooking element has a terminal tooth configured to be snap-fittingly housed in a corresponding transversely projecting section of the cavity of the closure cap, so as to achieve an unmovable coupling between the tamper-proof insert and the closure cap.

In an embodiment, the tamper-proof insert comprises two longitudinal sections that are connected therebetween by the transverse section and a pair of terminal elements, each connected to a free end of a respective longitudinal section by a frangible connection, the terminal elements being configured to be housed in corresponding grooves formed on the external surface of the Luer-lock connector.

In an embodiment, the at least one unmovable coupling element comprises a pair of unmovable coupling elements, which are suitably spaced therebetween and each immovably housable in a corresponding cavity of the closure cap.

In an embodiment, the tamper-proof insert comprises two pairs of unmovable coupling elements, the unmovable coupling elements of each pair being opposed and suitably spaced therebetween, each pair being immovably housable in a corresponding cavity of the closure cap.

In an embodiment, the unmovable coupling means comprise a layer of glue applied between the tamper-proof insert and the closure cap.

In an embodiment, the unmovable coupling means consist of welding points or continuous welding applied between the tamper-proof insert and the closure cap.

In an embodiment, the frangible connection between the free end of each longitudinal section and the respective terminal element of the tamper-proof insert consists of a narrowing having a smaller section than that of the transverse section and the terminal elements of the tamper-proof insert.

In an embodiment, each groove of the Luer-lock connector has side and bottom walls which are inclined towards the inside of the groove and a chamfered inlet open end, opposite to the bottom wall.

In an embodiment, each terminal element of the tamper-proof insert has tapered edges which, when the terminal elements are inserted into the grooves of the Luer-lock connector, cooperate with the corresponding inclined side and bottom walls of the longitudinal grooves. In this way, the terminal elements of the tamper-proof insert are held within the grooves formed at the Luer-lock connector of the syringe, so that they are prevented from being lifted, either intentionally or unintentionally, in order to separate the tamper-proof insert from the cap, without causing a breakage in the frangible weakening zones.

In an embodiment, an annular surface, preferably normal to the longitudinal axis of the closure cap and which is designed to come into abutment against a corresponding annular surface of the Luer-lock connector, preferably normal to the longitudinal axis of the Luer-lock connector is delimited between the handle portion and the coupling portion of the closure cap.

In an embodiment, the tamper-proof cap further comprises a rubber housed in an axial cylindrical cavity of the closure cap, wherein the rubber has a first surface, a second surface, opposite to the first surface and facing an opening of the axial cavity so as to abut, in use, against a free end of the hollow tip of the syringe, and a side surface.

In an embodiment, at least one, preferably a series of longitudinal grooves is formed at the side surface of the rubber.

In an embodiment, the first surface of the rubber is plane or convex, with convexity facing the hollow tip of the syringe.

In an embodiment, two recesses are further formed in the handle portion, which extend substantially for the entire length of the handle portion and are arranged on opposite sides with respect to the external seat for housing the tamper-proof insert.

In an embodiment, the tamper-proof insert has a different colour from that of the closure cap. This advantageously allows a rapid and immediate identification of the tamper-proof insert, and therefore of the integrity thereof or not, by a user of the syringe.

Further features and advantages of the present invention will be more evident from the following description.

BRIEF DESCRIPTION OF THE DRAWINGS

The invention will be described hereinbelow with reference to certain examples provided by way of non-limiting example and illustrated in the accompanying drawings. These drawings illustrate different aspects and embodiments of the present invention and reference numerals illustrating structures, components, materials and/or similar elements in different drawings are indicated by similar reference numerals, where appropriate.

DETAILED DESCRIPTION OF THE EMBODIMENTS

Figure 1:
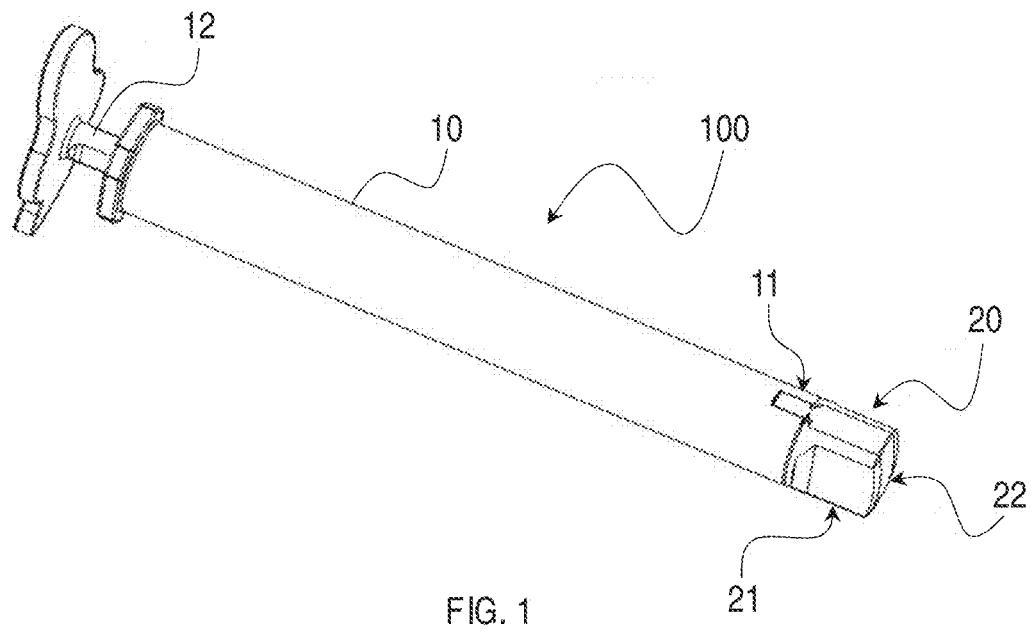
FIG. 1 is a perspective view of a syringe with Luer-lock connector equipped with tamper-proof cap according to the present invention.

While the invention is susceptible to various modifications and alternative constructions, certain preferred embodiments are shown in the drawings and are described hereinbelow in detail. It must in any case be understood that there is no intention to limit the invention to the specific embodiment illustrated, but, on the contrary, the invention intends covering all the modifications, alternative and equivalent constructions that fall within the scope of the invention as defined in the claims.

The use of "for example", "etc.", "or" indicates non-exclusive alternatives without limitation, unless otherwise indicated. The use of "includes" means "includes, but not limited to" unless otherwise indicated.

With reference to FIG. 1, it is therein illustrated a syringe with Luer-lock connector equipped with tamper-proof cap according to a preferred embodiment of the present invention.

The syringe, generally indicated by reference number 100, is preferably a pre-filled syringe and comprises a hollow cylindrical body 10, typically transparent, containing a product to be injected, and a plunger 12, sliding inside the hollow cylindrical body 10.

Figure 2:
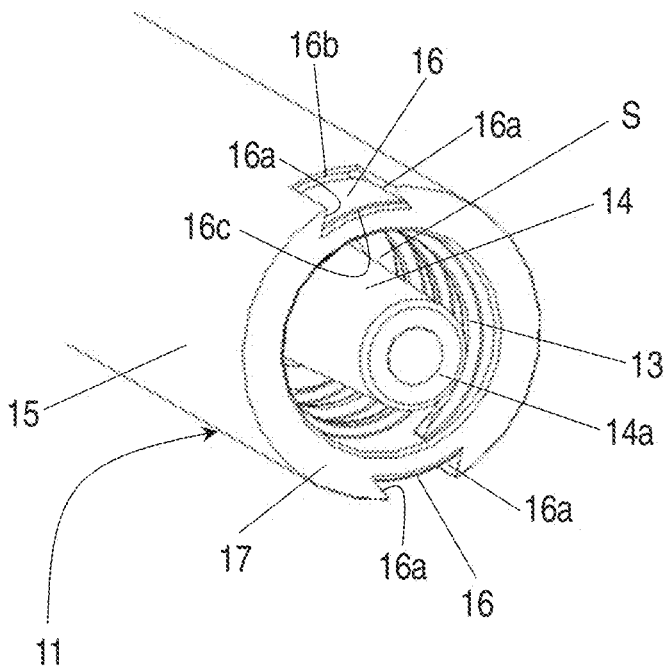
FIG. 2 is a perspective view of the Luer-lock connector of the syringe of FIG. 1, with the grooves for the insertion of the terminal elements of the tamper-proof insert highlighted.

As shown in FIG. 2, a hollow and substantially frusto-conical tip 14, onto which a needle (not shown) is subsequently fitted for the injection of the product present in the cylindrical body 10, extends from the hollow cylindrical body 10. At the tip 14 there is a Luer-lock connector 11 provided with an internal threading 13. A space S is delimited between the Luer-lock connector 11 and the tip 14.

Two longitudinal grooves 16, preferably diametrically opposite therebetween, are also formed on an external surface 15 of the Luer-lock connector 11, precisely at one free end of the Luer-lock connector, the function of which will become clearer in the following of this description. Alternatively, and without departing from the scope of the present invention, only one longitudinal groove 16 can be provided.

Each groove 16 has side 16*a* and bottom 16*b* walls, preferably inclined towards the inside of the groove 16 to form slots. Each groove 16 also has an open end 16*c*, opposite to the bottom surface 16*b*, for entering each groove 16. The open end 16*c* is preferably chamfered.

With reference again to FIG. 1, the syringe 100 is closed by a tamper-proof cap 20, which comprises a closure cap 21 and a tamper-proof insert 22, which can be immovably coupled therebetween.

Figure 3:
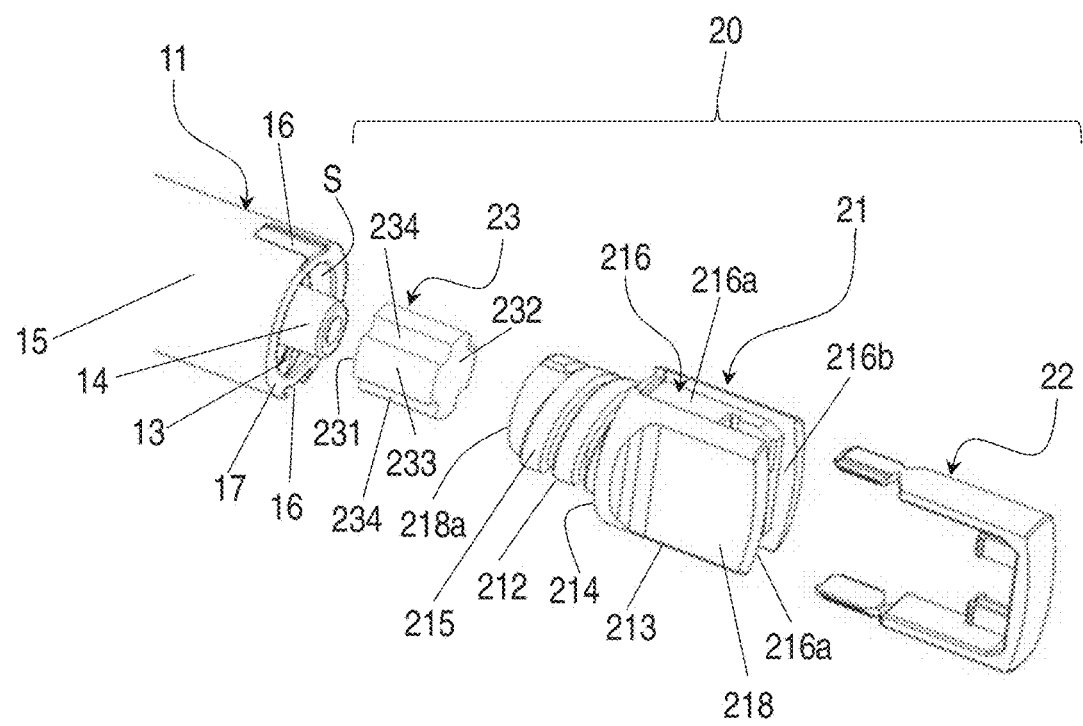
FIG. 3 is an exploded and partial perspective view of the syringe of FIG. 1.
Figure 4:
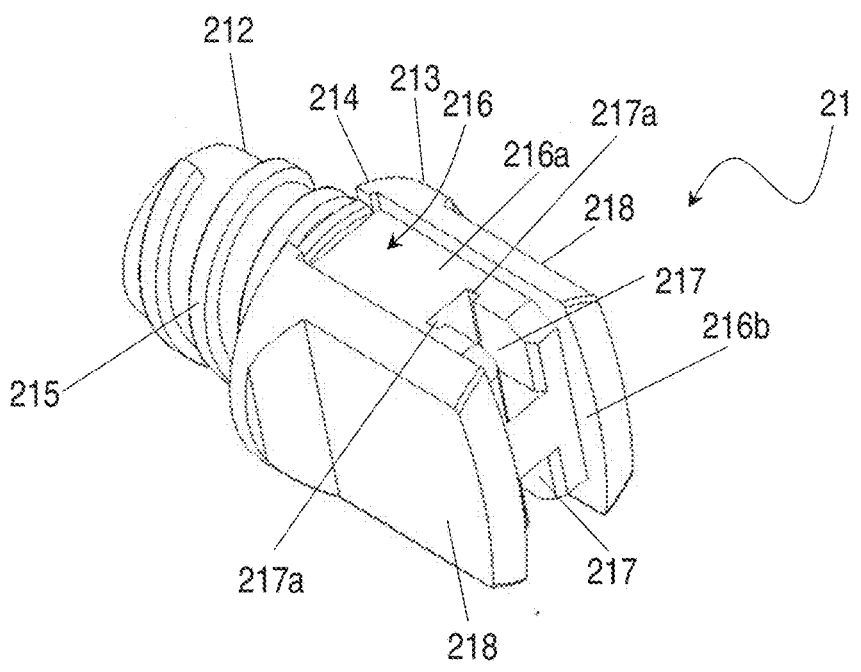
FIG. 4 is a perspective view of the tamper-proof cap of the syringe of FIG. 1, without the tamper-proof insert.
Figure 5:
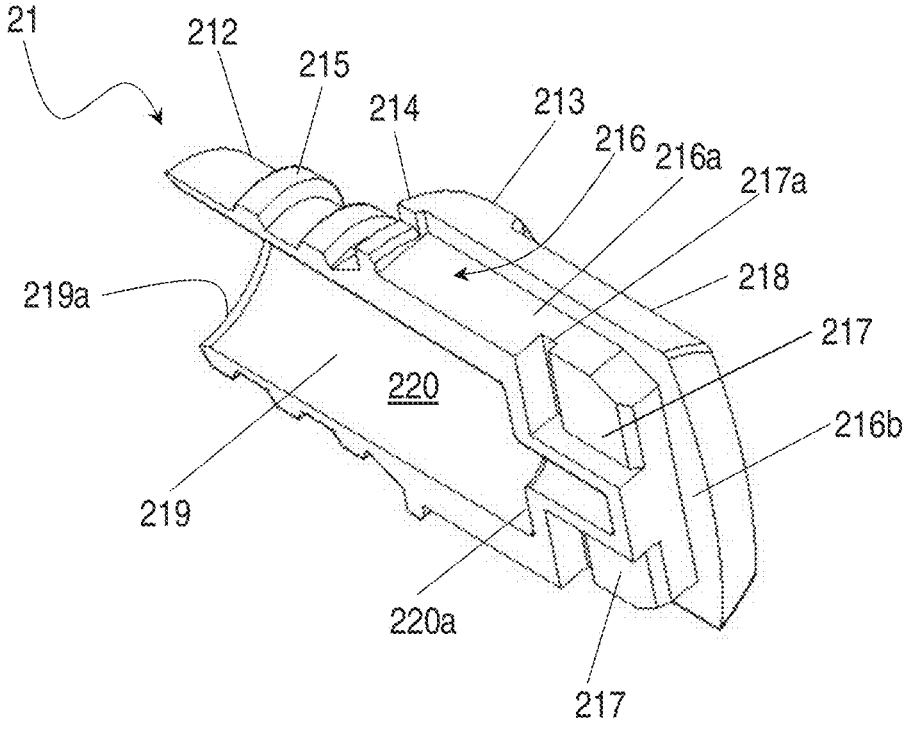
FIG. 5 is a longitudinal sectional view of the cap of FIG. 4.

As shown in detail in FIGS. 3 to 5, the closure cap 21 comprises a substantially cylindrical portion 212 for coupling with the Luer-lock connector 11 of the syringe 100 and a handle portion 213, it also being substantially cylindrical.

The coupling portion 212 has an external diameter smaller than the external diameter of the handle portion 213, whereby an annular surface 214, preferably normal to the longitudinal axis of the closure cap 21, is delimited between the handle portion 213 and the coupling portion 212. When the closure cap 21 is fitted onto the syringe 100, the annular surface 214 is designed to come into abutment against a corresponding annular surface 17 of the Luer-lock connector 11, preferably normal to the longitudinal axis of the Luer-lock connector 11. As will be described in detail below, the presence of the annular surfaces 214 and 17, which achieve the mechanical abutment, is particularly advantageous when assembling the tamper-proof cap 20 onto the syringe 100.

The coupling portion 212 also has an external threading 215 for coupling with the internal threading 13 of the Luer-lock connector 11 of the syringe 100.

The handle portion 213 has an external seat 216 for housing the tamper-proof insert 22. In particular, the external seat 216 is U-shaped and has two longitudinal sections 216*a*, formed on a side surface of the handle portion 213 and preferably opposed therebetween with respect to a plane passing through the longitudinal axis of the closure cap 21, and a transverse section 216*b*, for the connection between the longitudinal sections 216*a*, which is formed on an upper surface of the handle portion 213.

At the junction area between each longitudinal section 216*a* and the transverse section 216*b* of the external U-shaped seat 216, respective cavities 217 are also formed, which are designed to house corresponding elements for the unmovable coupling of the tamper-proof insert 22 to the closure cap 21. In particular, each cavity 217 extends longitudinally towards the inside of the handle portion 213 of the closure cap 21 and ends with at least one, preferably two sections 217*a*, projecting transversely from both parts of the cavity 217 and the function of which will become clearer in the following of the present description. Alternatively, each cavity 217 is free of the projecting sections 217*a* and preferably has slightly inclined walls, so as to snap fit a parallelepiped-shaped pin inserted therein.

Alternatively, and without departing from the scope of the present invention, it is possible to provide an external seat 216 having a single longitudinal section and a single cavity 217 at the junction area between the longitudinal section and the transverse section of the external seat 216.

Two recesses 218 are further formed in the side surface of the handle portion 213, which form two flat faces, parallel and symmetrical with respect to the plane passing through the longitudinal axis of the closure cap 21. The recesses 218 extend substantially for the entire length of the handle portion 213 and are arranged at opposite sides with respect to a longitudinal plane and normal to the longitudinal sections 216*a* of each external seat 216. The recesses 218 are specular to each other with respect to the plane normal to the longitudinal axis of the closure cap 21 and have the function of accommodating the fingers of a user to facilitate the operation of unscrewing the tamper-proof cap 20 from the syringe 100. As an alternative to the recesses 218, a smooth
or faceted external surface can be provided.

As clearly visible in FIG. 5, an axial cavity 219, it being
also substantially cylindrical, having an opening 219a at the
coupling portion 212 is formed in the closure cap 21. The
axial cylindrical cavity 219 also has a side surface 220 and
an upper surface 220a.

With reference again to FIG. 3, the closure cap 21
preferably comprises a rubber 23, which is housed in the
axial cylindrical cavity 219.

The rubber 23 is substantially cylindrical in shape and has
a first surface 231, a second surface 232, opposite to the first
surface 231, and a side surface 233. The first surface 231
faces the opening 219a of the axial cavity 219, so as to abut,
in use, against a free end 14a (FIG. 2) of the tip 14 of the
syringe 100, while the second surface 232 abuts, in use,
against the upper surface 220a of the axial cylindrical cavity
219 of the closure cap 21.

The first surface 231 and the second surface 232 are
preferably plane, while at least one, preferably a series of
longitudinal grooves 234 is formed at the side surface 233,
which allow the user to deform the rubber 23 to facilitate,
advantageously, the insertion thereof into the axial cylindri-
cal cavity 219 of the closure cap, during assembly of the
tamper-proof cap 20. The longitudinal grooves 234 also
advantageously favour the leakage of air during the insertion
of the rubber 23 into the axial cylindrical cavity 219, during
the assembly of the tamper-proof cap 20, so that no air
remains trapped between the upper surface 220a of the axial
cylindrical cavity 219 and the second surface 232 of the
rubber 23.

The first surface 231 of the rubber 23 designed to abut, in
use, against the tip 14 of the syringe 100 may be convex,
with convexity facing the tip 14. In this case, as the
tamper-proof cap 20 is screwed onto the syringe 100, the
first convex surface 231 of the rubber 23 flattens, thus
abutting against the tip 14 of the syringe 100, air-tightly
closing the opening thereof.

Figure 6:
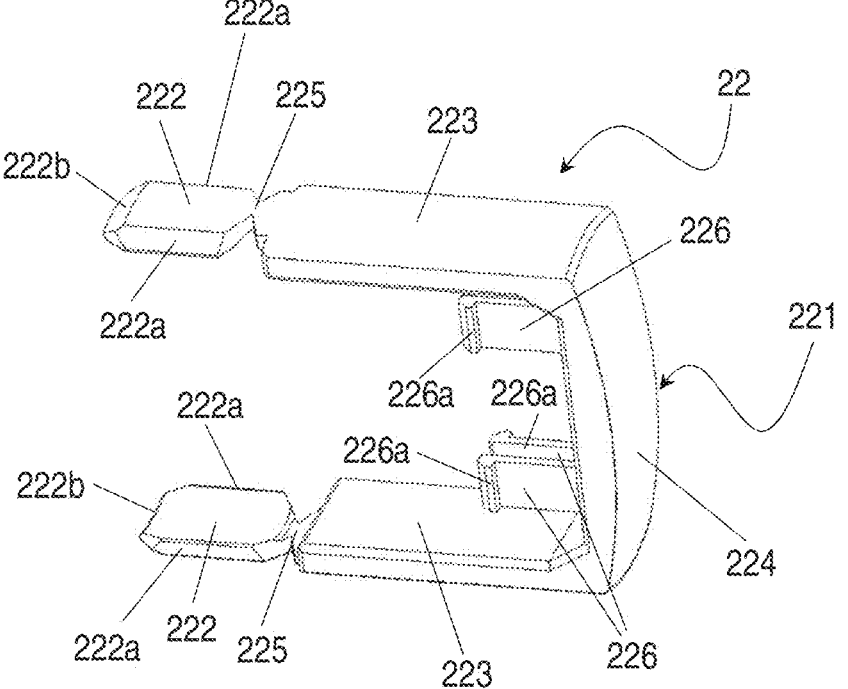
FIG. 6 is a perspective view of the tamper-proof insert of the syringe according to the present invention.
Figure 7:
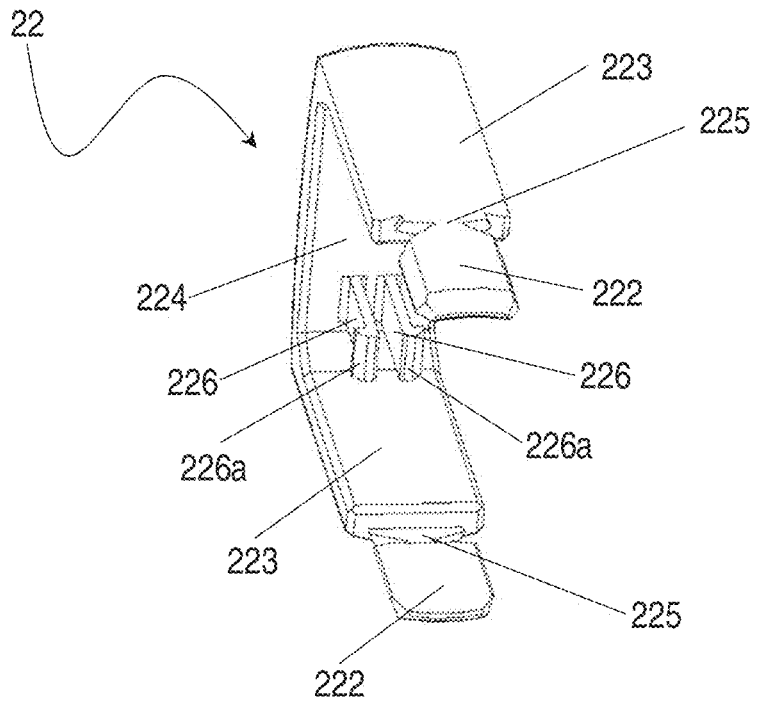
FIG. 7 is a perspective view, taken from another angle, of the tamper-proof insert of FIG. 6.

With reference in particular to FIGS. 6 and 7, the tamper-
proof insert 22 comprises a main body 221, whose shape is
complementary to that of the external seat 216 of the handle
portion 213 and configured to be immovably coupled with
the closure cap 21, so as to form a single body with it.

The tamper-proof insert may be immovably housed, for
example glued or welded, for example by ultrasonic weld-
ing, inside the external seat 216, so as to form a single body
with the closure cap 21. By way of example, the unmovable
coupling between the tamper-proof insert 22 and the closure
cap 21 is achieved by applying a layer of glue between the
external seat 216 of the handle portion 213 of the closure cap
21 and a respective longitudinal section 223 of the tamper-
proof insert 22 or between one or more of the unmovable
coupling elements 226 and the corresponding housing cavity
217.

The tamper-proof insert 22 further comprises at least one
terminal element, preferably a pair of terminal elements 222,
each configured to engage immovably with a corresponding
longitudinal groove 16 of the Luer-lock connector 11. Pref-
erably, each terminal element 222 has tapered edges 222a
and 222b, which, when the terminal element is inserted into
the corresponding longitudinal groove, cooperate with cor-
responding inclined side 16a and bottom 16b walls of the
longitudinal groove, so as to prevent the terminal element
from being lifted without causing it to break, which would
signal to the user of the syringe 100 that the tamper-proof
cap 20 has been tampered with.

Similar to the external seat 216 of the handle portion 213
of the closure cap 21, the main body 221 of the tamper-proof
insert 22 comprises at least one, preferably two longitudinal
sections 223 and a transverse section 224, for the connection
between the longitudinal sections 223. Each terminal ele-
ment of the pair of terminal elements 222 extends from a
free end of a corresponding longitudinal section 223 and is
connected thereto by a frangible connection 225, preferably
consisting of a narrowing having a smaller section than that
of the longitudinal section 223 and the terminal element 222.

From a central area of the transverse section 224 of the
tamper-proof insert 22 there extends, towards the inside of
the tamper-proof insert 22 and in proximity to a respective
longitudinal section 223 of the tamper-proof insert 22, at
least one means for the unmovable coupling of the tamper-
proof element 22 to the closure cap 21, having the shape of
a hooking element 226, preferably of two hooking elements
226, even more preferably of two pairs of hooking elements
226. The hooking elements 226 of each pair extend, opposed
and suitably spaced therebetween, transversely to the
respective longitudinal section 223 of the tamper-proof
insert 21.

Each hooking element 226 is designed to be housed in a
corresponding cavity 217 of the closure cap 21 and has a
terminal tooth 226a configured to be snap-fittingly housed in
a corresponding transversely projecting section 217a of the
cavity 217, so as to achieve an unmovable coupling between
the tamper-proof insert 22 and the closure cap 21.

Alternatively, the unmovable coupling means consist of
one or more unmovable coupling elements, each configured
to be coupled by interference with the corresponding cavity
217 of the closure cap. For this purpose, the unmovable
coupling element is wedge-shaped or the respective cavity
217 of the closure cap 21 has slightly inclined walls, so as
to snap fit a parallelepiped-shaped pin inserted therein.

When the tamper-proof insert 22 is immovably coupled to
the closure cap 21, the hooking elements 226 are internal to
the tamper-proof cap 20 and therefore not accessible from
the outside. This makes it advantageously impossible to
separate the tamper-proof insert 22 from the closure cap 21,
for example as a result of elastic deformation of the hooking
elements 226, for tampering purposes.

Furthermore, since the main body 221 of the tamper-proof
insert 22 is complementary in shape to that of the external
seat 216 of the handle portion 213 of the closure cap 21, the
tamper-proof insert 22, when immovably coupled to the
closure cap 21, forms a single outline with the latter, so that
the tamper-proof cap 20 does not have, in the handle portion
213, unsightly and annoying projecting parts. As well as
being advantageous in terms of aesthetics and functionality,
this aspect allows, when filling the syringe 100 with a drug
product, to use the same supports used for syringes that use
caps without tamper-proof inserts and oversized tamper-
proof systems in general.

Preferably, the colour of the tamper-proof insert 22 is
different from that of the closure cap 21, for example red in
colour. This allows a rapid and immediate identification of
the tamper-proof insert, and therefore of the integrity thereof
or not, by a user of the syringe.

The closure cap 21 and the tamper-proof insert 22 are
preferably made of a non-flexible plastic material, for
example compact polycarbonate (Makrolon®), cyclic-olefin
polymer (COP), or cyclic-olefin copolymer (COC).

Figure 8:
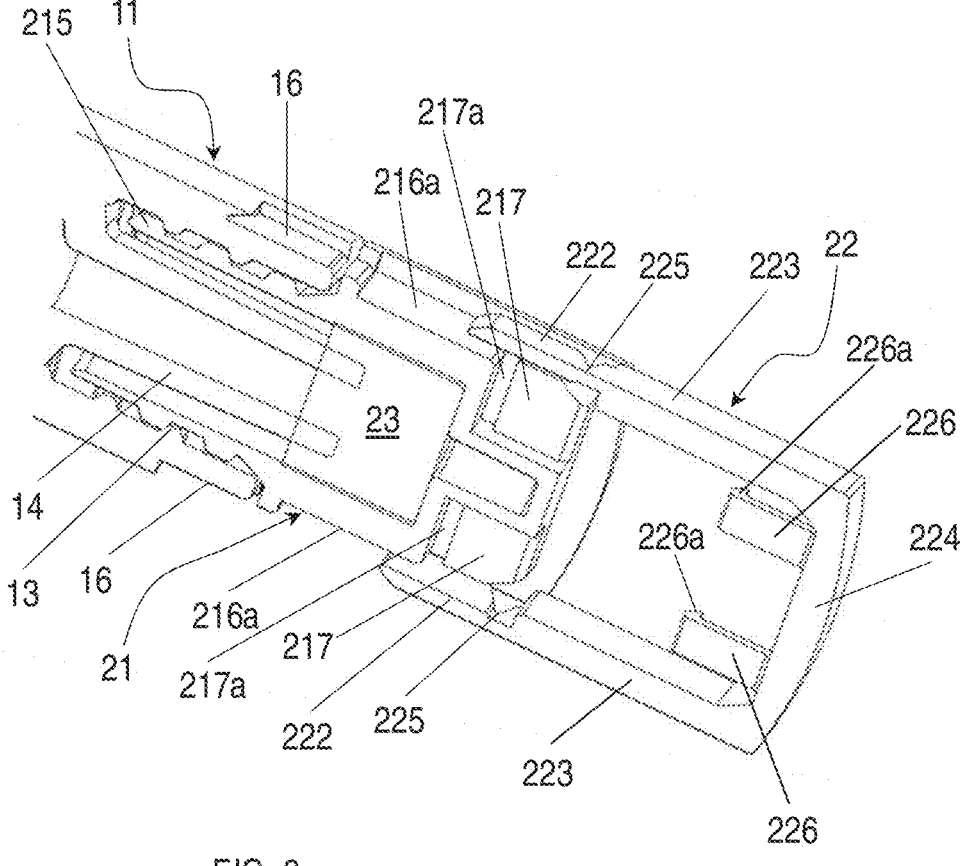
FIG. 8 is a sectional and partial perspective view of the tamper-proof cap, with the closure cap coupled to the syringe and the tamper-proof insert being coupled with the closure cap.
Figure 9:
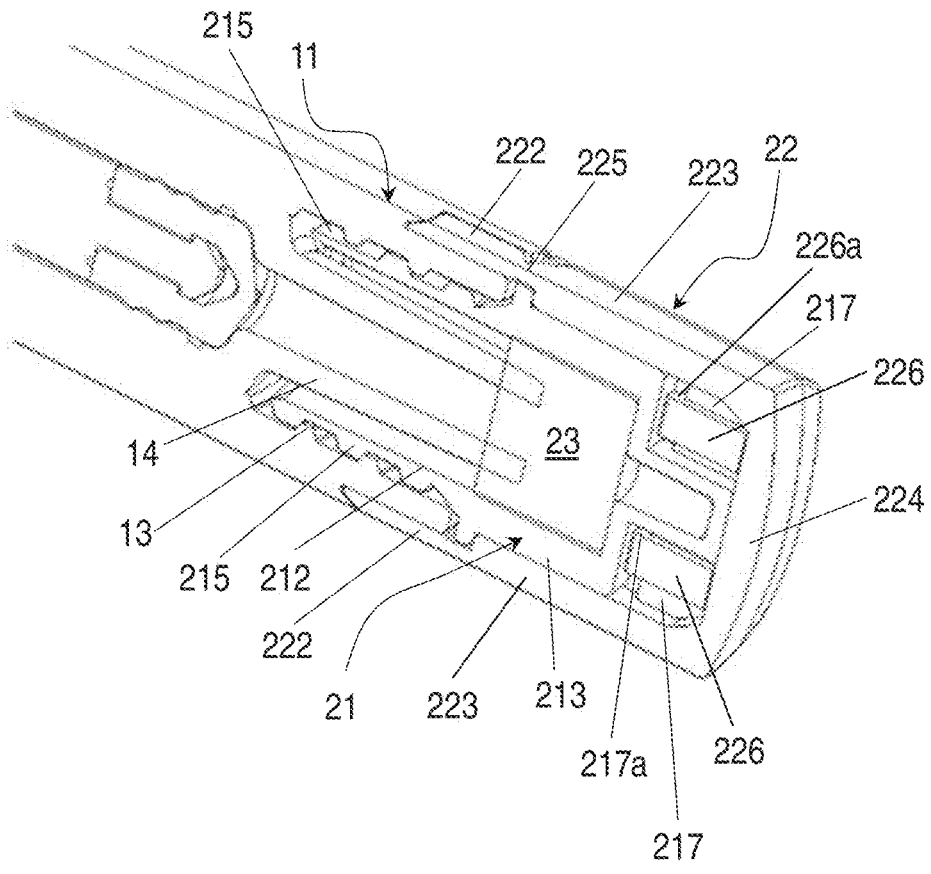
FIG. 9 is a perspective view, similar to that of FIG. 8, with the tamper-proof insert immovably coupled to the closure cap and to the Luer-lock connector of the syringe.

With reference to FIGS. 8 and 9, the method for the
manual and automatic assembly of the tamper-proof cap 20
onto the syringe 100 is now described.

In the manual assembly phase, the closure cap 21 is first screwed onto the Luer-lock connector 11 of the syringe 100, by coupling the external threading 215 of the coupling portion 212 with the internal threading 13 of the Luer-lock connector 11, until each longitudinal section 216a of the external seat 216 of the coupling portion 212 is aligned with the corresponding groove 16 of the Luer-lock connector 11.

Otherwise, in the case of automatic assembly, for example by means of an automatic screwing system, the closure cap 21 is screwed onto the Luer-lock connector 11 of the syringe 100, by coupling the external threading 215 of the coupling portion 212 with the internal threading 13 of the Luer-lock connector 11, until the annular surface 214 of the coupling portion 212 is brought into abutment against the corresponding annular surface 17 of the Luer-lock connector. At this point, the automatic screwing system detects a sudden increase in the torque required for screwing, and this indicates that the so-called mechanical "zero" has been reached, from which the mechanical screwing system moves on unscrewing the closure cap 21 by a predetermined angle, so as to bring each longitudinal section 216a of the external seat 216 of the coupling portion 212 into alignment with the corresponding groove 16 of the Luer-lock connector 11, while ensuring that the syringe 100 is hermetically closed.

If the rubber 23 is present, before screwing the closure cap 21 onto the Luer-lock connector 11 of the syringe 100, the rubber 23 is inserted inside the axial cylindrical cavity 219 of the closure cap 21 until the second surface 232 of the rubber 23 is brought into abutment with the upper surface 220a of the axial cylindrical cavity 219. In such a case, at the end of screwing the closure cap 21 onto the Luer-lock connector 11, the first surface 231 of the rubber 23 is in abutment against the free end 14a of the tip 14 of the syringe 100.

Once the closure cap 21 has been screwed onto the Luer-lock connector 11, with each longitudinal section 216a of the external seat 216 of the coupling portion 212 in alignment with the corresponding groove 16 of the Luer-lock connector 11, the tamper-proof insert 22 is mounted on the closure cap 21.

For this purpose, and as shown in FIG. 8, the tamper-proof insert 22 is fitted onto the external seat 216 of the closure cap 21 and slid inside the external seat 216, so as to establish an unmovable coupling between the tamper-proof insert 22 and the closure cap 21.

In particular, if unmovable coupling elements are provided, these are housed, either by interference or by snap-fit, in the respective cavity 217 of the closure cap.

With particular reference to the hooking elements 226, when the tamper-proof insert 22 is fitted onto the closure cap 21, the terminal hooking teeth 226a of the hooking elements 226 of the tamper-proof insert 22 are snap-fittingly housed, by elastic deformation, in the corresponding transversely projecting sections 217a of the cavities 217 present inside the closure cap 21 and the terminal elements 222 of the tamper-proof insert 22 are housed, also immovably, inside the longitudinal grooves 16 of the Luer-lock connector 11.

Precise insertion, and subsequent sliding without breakage, of the terminal elements 222 into the longitudinal grooves 16 is ensured by the chamfered open end 16c of the longitudinal grooves 16 and by the cooperation of the tapered edges 222a and 222b of the terminal elements 222 with the corresponding inclined side 16a and bottom 16b walls and of the longitudinal grooves 16.

FIG. 9 illustrates the tamper-proof cap 20 in its operating, tight-closure and tamper-proof position on the Luer-lock connector 11 of the syringe 100.

It is assumed, now, that one wishes to decouple the tamper-proof cap 20 from the syringe 100. The user, typically a healthcare professional who has to inject the drug product contained in the hollow cylindrical body 10 of the syringe 100 into a patient's body, proceeds to unscrew the tamper-proof cap 20.

Since the terminal elements 222 of the tamper-proof insert 22 are immovably housed within the longitudinal grooves 16 of the Luer-lock connector 11, the rotation of the tamper-proof cap 20 with respect to the Luer-lock connector 11 causes the frangible connections 225 between the terminal elements 222, fixed, and the corresponding longitudinal sections 223, rotatingly movable, of the tamper-proof insert 22 to break.

The breakage of the frangible connections 225 therefore causes the assembly closure cap 21 and tamper-proof insert 22—deprived of its terminal elements 222—to separate from the Luer-lock connector 11 and the syringe 100 to open.

From the foregoing, it is understood that the only way to separate the tamper-proof insert 22 from the closure cap 21 is to break the frangible connections 225 of the tamper-proof insert 22, so that, if the tamper-proof cap 20 had been tampered with, the user of the syringe 100 would immediately notice that it had been broken, thus immediately detecting the evidence of tampering.

It should also be noted that it is not possible for an external subject to tamper with the tamper-proof cap 20, i.e. to decouple the tamper-proof cap 20 from the Luer-lock connector 11, without breaking the tamper-proof insert 22 at the appropriate frangible connections 25. In fact, the elements 226 for the unmovable coupling between the tamper-proof insert 22 and the closure cap 21 are internal to the tamper-proof cap 20 and cannot be accessed from the outside and are therefore impossible to violate.

From the description made, the characteristics of the syringe with Luer-lock connector equipped with tamper-proof cap of the present invention are clear, as are the advantages thereof.

The invention thus conceived is susceptible to several modifications and variations, all falling within the scope of the inventive concept.

The invention claimed is:

1. A syringe, comprising:
   a hollow cylindrical body containing a product to be injected and from which a hollow tip equipped with a Luer-lock connector extends, and a plunger configured to slide inside the hollow cylindrical body; and
   a tamper-proof cap comprising a closure cap and a tamper-proof insert, wherein the closure cap includes a portion for coupling with the Luer-lock connector and a handle portion;
   wherein an external seat for housing the tamper-proof insert is formed in the handle portion of the closure cap,
   wherein the tamper-proof insert comprises at least one longitudinal section, a transverse section and a terminal element which is connected to a free end of the longitudinal section by a frangible connection, the terminal element configured to be immovably housed in a corresponding groove formed on an external surface of the Luer-lock connector,
   and wherein the tamper-proof cap further comprises means for the unmovable coupling of the tamper-proof insert and the closure cap.

2. The syringe according to claim 1, wherein the unmovable coupling means comprises at least one element for the unmovable coupling to the handle portion of the closure cap, wherein the at least one coupling element extends from the transverse section of the tamper-proof insert towards the inside of the tamper-proof insert, in order to be coupled by interference with a corresponding cavity of the closure cap, which extends towards the inside of the handle portion of the closure cap.

3. The syringe according to claim 2, wherein at least the at least one unmovable coupling element is wedge-shaped or the corresponding cavity of the closure cap has slightly inclined walls.

4. The syringe according to claim 2, wherein the unmovable coupling means comprise at least one hooking element which extends from the transverse section of the tamper-proof insert towards the inside of the tamper-proof insert, in order to be snap-fittingly housed in a corresponding cavity of the closure cap, which extends towards the inside of the handle portion of the closure cap.

5. The syringe according to claim 4, wherein the hooking element has a terminal tooth configured to be snap-fittingly housed in a corresponding transversely projecting section of the cavity, thereby providing an unmovable coupling between the tamper-proof insert and the closure cap.

6. The syringe according to claim 1, wherein the tamper-proof insert comprises two longitudinal sections which are connected therebetween by the transverse section and a pair of terminal elements, each connected to a free end of a respective longitudinal section by a frangible connection, wherein the terminal elements are configured to be housed in corresponding grooves formed on the external surface of the Luer-lock connector.

7. The syringe according to claim 1, wherein the at least one unmovable coupling element comprises a pair of unmovable coupling elements, suitably spaced therebetween and each immovably housable in a corresponding cavity of the closure cap.

8. The syringe according to claim 1, wherein the at least one unmovable coupling element comprises two pairs of unmovable coupling elements, wherein the unmovable coupling elements of each pair are opposed and suitably spaced therebetween, each pair of unmovable coupling elements immovably housable in a corresponding cavity of the closure cap.

9. The syringe according to claim 1, wherein the unmovable coupling means comprises a layer of glue applied between the tamper-proof insert and the closure cap.

10. The syringe according to claim 1, wherein the unmovable coupling means comprises welding points or continuous welding applied between the tamper-proof insert and the closure cap.

11. The syringe according to claim 1, wherein the frangible connection between the free end of each longitudinal section and the respective terminal element of the tamper-proof insert comprises a narrowing having a smaller section than that of the transverse section and the terminal element of the tamper-proof insert.

12. The syringe according to claim 1, wherein each groove of the Luer-lock connector has side and bottom walls, each of which are inclined towards the inside of the groove and a chamfered inlet open end, opposite to the bottom wall.

13. The syringe according to claim 6, wherein each terminal element of the tamper-proof insert has tapered edges which, when the terminal elements are inserted into the grooves of the Luer-lock connector, cooperate with the corresponding inclined side and bottom walls of the grooves.

14. The syringe according to claim 1, wherein an annular surface, which is designed to come into abutment against a corresponding annular surface of the Luer-lock connector, is delimited between the handle portion and the coupling portion of the closure cap.

15. The syringe according to claim 1, wherein the tamper-proof cap further comprises a rubber housed in an axial cylindrical cavity of the closure cap, wherein the rubber has a first surface, a second surface opposite to the first surface and facing an opening of the axial cylindrical cavity so as to abut, in use, against a free end of the hollow tip of the syringe, and a side surface.

16. The syringe according to claim 15, wherein at least one longitudinal groove is formed at the side surface of the rubber.

17. The syringe according to claim 15, wherein the first surface of the rubber is plane or convex with convexity facing the hollow tip of the syringe.

18. The syringe according to claim 1, wherein two recesses are further formed in the handle portion, and the recesses extend substantially for the entire length of the handle portion and are arranged on opposite sides with respect to the external seat for housing the tamper-proof insert.

19. The syringe according to claim 1, wherein the tamper-proof insert has a different colour from that of the closure cap.

* * * * *